US011832866B2

(12) United States Patent
Bharat et al.

(10) Patent No.: US 11,832,866 B2
(45) Date of Patent: Dec. 5, 2023

(54) SYSTEM AND METHOD FOR ADAPTIVE ABLATION AND THERAPY BASED ON ELASTOGRAPHY MONITORING

(71) Applicant: KONINKLIJKE PHILIPS N.V., Eindhoven (NL)

(72) Inventors: Shyam Bharat, Arlington, MA (US); Ajay Anand, Fishkill, NY (US); Shriram Sethuraman, Woburn, MA (US); Sheng-Wen Huang, Ossining, NY (US); William Tao Shi, Wakenfield, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 60 days.

(21) Appl. No.: 15/550,194

(22) PCT Filed: Feb. 16, 2016

(86) PCT No.: PCT/IB2016/050806
§ 371 (c)(1),
(2) Date: Aug. 10, 2017

(87) PCT Pub. No.: WO2016/135584
PCT Pub. Date: Sep. 1, 2016

(65) Prior Publication Data
US 2018/0271577 A1    Sep. 27, 2018

Related U.S. Application Data
(60) Provisional application No. 62/121,520, filed on Feb. 27, 2015.

(51) Int. Cl.
*A61B 8/08*    (2006.01)
*A61B 18/00*    (2006.01)
(Continued)

(52) U.S. Cl.
CPC ............... *A61B 18/00* (2013.01); *A61B 8/08* (2013.01); *A61B 8/485* (2013.01); *A61B 18/12* (2013.01);
(Continued)

(58) Field of Classification Search
CPC .............. A61B 8/085; A61B 8/5261; A61B 2018/00577; A61B 8/08; A61B 18/12; A61B 2017/0019
See application file for complete search history.

(56) References Cited

U.S. PATENT DOCUMENTS 7,166,075 B2    1/2007    Varghese et al.
7,306,593 B2    12/2007    Keidar et al.
(Continued)

FOREIGN PATENT DOCUMENTS

CN    103720489 A    4/2014
JP    2000175933 A    6/2000

*Primary Examiner* — Joseph A Stoklosa
*Assistant Examiner* — Annie L Shoulders

(57) ABSTRACT

A system for performing ablation includes an ablation device (102) configured to ablate tissue in accordance with control parameters and configured to make measurements during the ablation process. An imaging system (104) is configured to measure an elastographic related parameter to monitor ablation progress. A parameter estimation and monitoring module (115) is configured to receive the measurements from the ablation device and/or the elastographic related parameter to provide feedback to adaptively adjust imaging parameters of the imaging device at different times during an ablation process.

17 Claims, 7 Drawing Sheets

(51) Int. Cl.
   *A61B 34/10* (2016.01)
   *A61B 34/00* (2016.01)
   *A61B 90/00* (2016.01)
   *A61B 18/12* (2006.01)
   *A61B 17/00* (2006.01)

(52) U.S. Cl.
   CPC .............. *A61B 34/10* (2016.02); *A61B 34/25* (2016.02); *A61B 2017/0019* (2013.01); *A61B 2018/00577* (2013.01); *A61B 2018/00642* (2013.01); *A61B 2018/00684* (2013.01); *A61B 2018/00702* (2013.01); *A61B 2018/00779* (2013.01); *A61B 2018/00791* (2013.01); *A61B 2018/00886* (2013.01); *A61B 2090/378* (2016.02)

(56) References Cited

U.S. PATENT DOCUMENTS

| | | | |
|---|---|---|---|
| 7,871,406 B2 * | 1/2011 | Nields | A61B 18/1815 606/27 |
| 8,328,726 B2 | 12/2012 | Varghese et al. | |
| 8,556,888 B2 | 10/2013 | Nields et al. | |
| 9,034,004 B2 | 5/2015 | Pansky | |
| 9,480,414 B2 | 11/2016 | Popescu | |
| 10,556,132 B2 | 2/2020 | Tyler | |
| 2005/0215899 A1 * | 9/2005 | Trahey | A61B 5/0048 600/439 |
| 2007/0264625 A1 * | 11/2007 | DeBenedictis | A61B 18/203 435/4 |
| 2009/0149753 A1 * | 6/2009 | Govari | A61B 8/4254 600/439 |
| 2010/0036378 A1 * | 2/2010 | Savery | A61B 18/1206 606/42 |
| 2010/0069751 A1 * | 3/2010 | Hazard | G01S 7/52042 600/438 |
| 2010/0256530 A1 * | 10/2010 | Varghese | A61B 5/015 600/587 |
| 2010/0286520 A1 | 11/2010 | Hazard et al. | |
| 2011/0251529 A1 | 10/2011 | Petruzzello et al. | |
| 2012/0065506 A1 | 3/2012 | Smith | |
| 2012/0078102 A1 | 3/2012 | Lee | |
| 2012/0128223 A1 | 5/2012 | Hassan et al. | |
| 2012/0310064 A1 | 12/2012 | Mcgee | |
| 2015/0005633 A1 | 1/2015 | Kanayama et al. | |
| 2016/0113699 A1 * | 4/2016 | Sverdlik | A61N 7/022 606/27 |

* cited by examiner

SYSTEM AND METHOD FOR ADAPTIVE ABLATION AND THERAPY BASED ON ELASTOGRAPHY MONITORING

CROSS-REFERENCE TO PRIOR APPLICATIONS

This application is the U.S. National Phase application under 35 U.S.C. § 371 of International Application Serial No. PCT/IB2016/050806, filed on Feb. 16, 2016, which claims the benefit of U.S. Application Ser. No. 62/121,520, filed on Feb. 27, 2015. These applications are hereby incorporated by reference herein.

BACKGROUND

Technical Field

This disclosure relates to ablation systems, methods and instruments and more particularly to elastographic measurements for optimizing ablation in medical applications.

Description of the Related Art

Thermal ablation techniques provide an excellent alternative to major surgery, which can pose a risk even with the most experienced surgeon. These techniques are minimally invasive requiring only needles (e.g., radiofrequency (RF), cryotherapy and microwave ablation) or a non-invasive heat source such as using high intensity focused ultrasound (HIFU). In most of the procedures, the cancerous tissue is heated to above 60° C. and coagulated.

Radiofrequency ablation (RFA) is currently the only FDA approved minimally invasive heating therapy in the United States. It uses a probe with an active electrode tip through which a 460-500 kHz alternating electric current is conducted. The current propagates through the body to the grounding pads placed either on the back or the thigh of the patient. The current causes ionic agitation and frictional heating. Heat is then dissipated through thermal conduction to ablate the tumor.

RFA is frequently used to treat liver cancer. Current treatment protocols use the simplistic spherical ablation volume predicted from device manufacturers' specifications. The actual treatment volumes greatly deviate from this prediction, resulting in large recurrence rates (approximately 35%).

RFA is typically performed under ultrasound, computed tomography (CT) or magnetic resonance imaging (MRI) guidance. One common reason for the high recurrence rates is the inability to monitor and control ablation size to adequately kill the tumor cells. Real-time feedback to the clinician can currently be achieved with reasonable accuracy with magnetic resonance (MR) based temperature imaging. However, magnetic resonance imaging (MRI) is expensive and may not be readily available. Ultrasound is another modality that is commonly used for image guidance during placement of the needle. However, the only way it is currently used for monitoring treatment is by visualizing the hyperechoic lesions on a B-mode image. In most cases, the hyperechogenicity is due to the formation of microbubbles during RFA which is a temporary effect and poorly correlated with the lesion boundaries. Therefore, such visualization is only approximate and not a good indicator of the treatment efficacy.

SUMMARY

In accordance with the present principles, a system for performing ablation includes an ablation device configured to ablate tissue in accordance with control parameters and configured to make measurements during the ablation process. An imaging system is configured to measure an elastographic related parameter to monitor ablation progress. A parameter estimation and monitoring module is configured to receive the measurements from the ablation device and/or the elastographic related parameter to provide feedback to adaptively adjust imaging parameters of the imaging device at different times during an ablation process.

Another system for performing ablation includes an ablation device configured to ablate tissue in accordance with a control signal. An imaging system is configured to make elastographic measurements. A parameter estimation and monitoring module is configured to receive the elastographic measurements as feedback from the imaging device and to adjust the control signal to control the ablation device to achieve therapy goals based on the elastographic measurements.

A method for ablation includes positioning an ablation device and an ultrasound probe in a subject to begin ablation; generating measurement information as feedback during the ablation process including an elastographic related parameter, the measurement information including information from at least one of the ablation device and an ultrasound scanner; adaptively updating at least one of imaging parameters of the ultrasound scanner and/or a control signal of the ablation device in accordance with the feedback; and completing the ablation process when a treatment goal is achieved.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
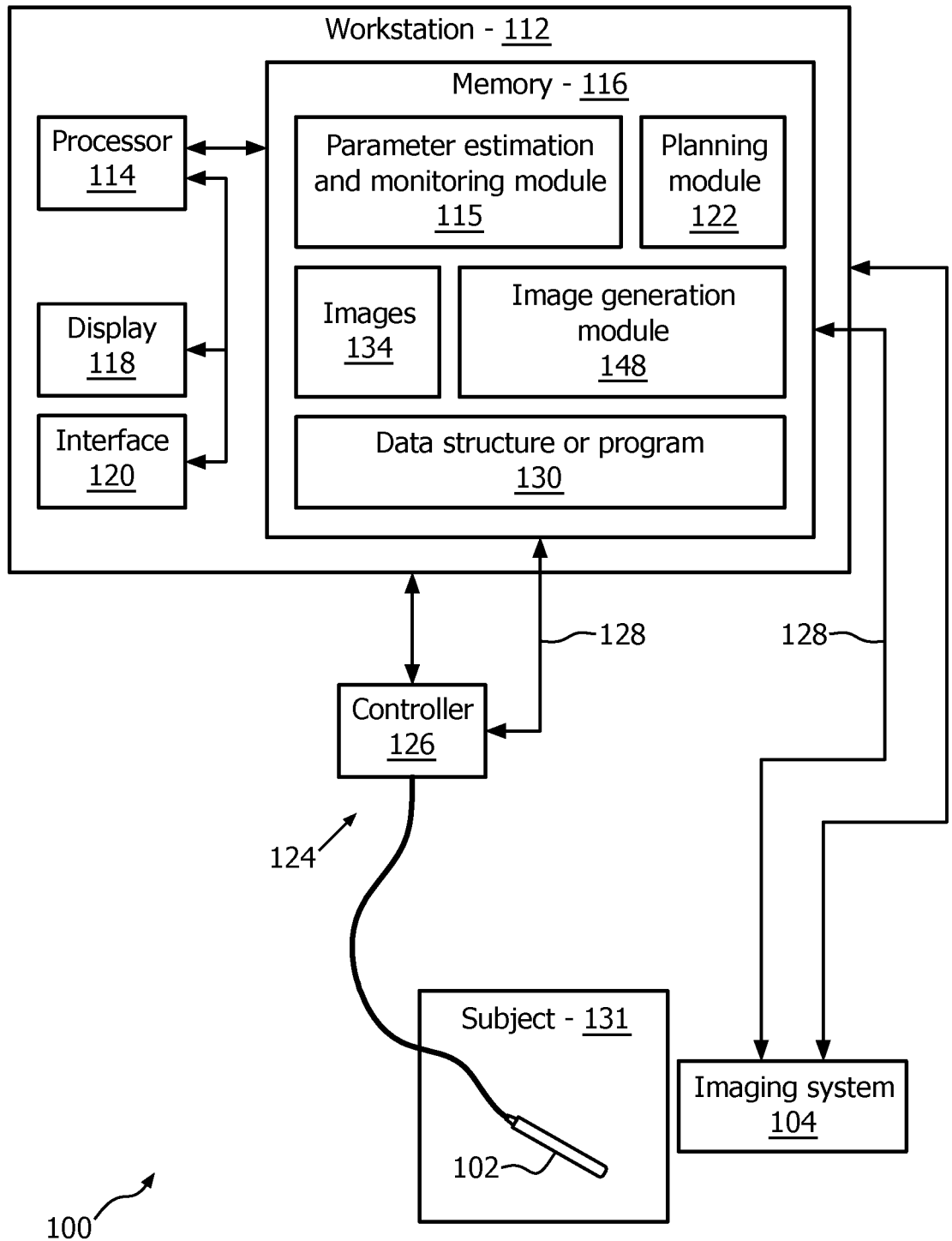
FIG. 1 is a block/flow diagram showing a system for performing ablation in accordance with useful embodiments.

In accordance with the present principles, a system, method and instruments are described for providing real-time feedback to a clinician or other operator during an ablation procedure. In particularly useful embodiments, the system, method and instruments employ shear wave elastography (SWE) as a modality for monitoring radiofrequency ablation (RFA) procedures. During RFA, the elastic properties of tissues change such that a region being ablated first turns softer and then progressively stiffer. SWE can resolve the extent of lesion formation during RFA, due to the dependence of the shear wave velocity on the underlying stiffness by determining changes in shear modulus during lesion formation. Different parameter sets for pushing and tracking the shear modulus or other shear wave or elasticity parameters at various stages of the lesion formation process may be provided.

In accordance with the present principles, the system, method and instruments provide for real-time optimization of the pushing and tracking pulse parameters to permit more accurate and reliable monitoring of the RFA procedure by enabling more accurate estimation of velocity and shear modulus. The RFA treatment may be controlled based on the estimated shear modulus to achieve complete tumor destruction.

The present principles automatically vary parameters of pushing and tracking pulses, based on inputs from the RFA system. Thus, at all stages of RFA, reliable velocity estimates (and hence, shear modulus estimates) can be obtained. The present systems include a communication link (or feedback loop) between the RFA system and the ultrasound (US) system. The parameters that are optimized in real-time may include but are not limited to: pulse repetition frequency (PRF), number of track locations, spacing between the tracking beams, etc. For example, at the beginning of the RFA procedure, a parameter vector 'X' may be utilized. From the RFA time elapsed (and/or output power/voltage or other input), the parameter vector will be changed accordingly (first to 'Y', then to 'Z' and so on). The values for 'X', 'Y', 'Z', etc. may be empirically determined. An example of a link between the RFA and US systems may be an Ethernet cable, interfacing computer/circuit board, etc.

Shear modulus is an inherent property of tissue and a direct relationship with many tumors and the degree of tissue damage (necrosis) exists. Treatment-related decisions may be based on this parameter. Conventional RFA systems either work without any feedback or with limited feedback in the form of temperature at the tip of the RF probe or electrical impedance in the closed circuit. Both of these feedback methods are indirect and hence prone to be suboptimal at tracking the efficacy of treatment. For example, temperature at the probe tip may not be fully indicative of whether the entire tumor has been completely destroyed especially at the tumor margins which is the most common clinical cause of local recurrence. A more reliable basis for controlling the RFA treatment would be to base decisions on actual changes observed in the tissue (e.g., stiffness or modulus changes) for an automated adaptive treatment solution.

In one embodiment, an automated solution adapts the RFA treatment in real-time, based on estimated tissue parameters (e.g., shear modulus) during ablation. For example, ablated (fully necrotic) liver tissue has shear modulus of >20 kPa in comparison to that of a normal liver of about 5 kPa. The shear modulus can be estimated at any desired point in the tissue. By estimating the modulus at the lesion boundaries, decisions can be made to appropriately adapt the RFA treatment (e.g., increase ablation time, stop ablation, re-position RF probe(s) etc.). For example, if the estimated shear modulus at the intended lesion boundary is 10 kPa, it may be concluded that the tissue at that location is not fully necrotic and the RFA treatment can be extended until the estimated modulus becomes ~20 kPa. This embodiment can be enabled by a communication link from the US system to the RFA system. The shear modulus (and optionally, other related parameters) estimated by the US system will be communicated to the RFA system over this link, for use in adapting the treatment protocol.

It should be understood that the present invention will be described in terms of medical instruments; however, the teachings of the present invention are much broader and are applicable to any ablation systems or instruments. In some embodiments, the present principles are employed in tracking, treating or analyzing biological tissues. In particular, the present principles are applicable to procedures for treating or modifying biological tissues in all areas of the body such as the lungs, gastro-intestinal tract, excretory organs, liver, kidneys, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, a system 100 for performing ablation is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store at least a portion of a parameter estimation and monitoring module 115 configured to estimate/optimize imaging parameters for an imaging system 104 (e.g., for pushing and tracking parameters) and/or to estimate/optimize ablation parameters for an ablation instrument(s) 102 (e.g., activating or deactivating the ablation instruments 102). Feedback signals from an ultrasound (US) device or system 104 are employed to measure shear modulus, shear wave velocity, tissue elasticity or other characteristics at an imaged or treated location to provide real-time information regarding the progression and treatment areas during a procedure. The parameter estimation and monitoring module 115 may include software (e.g., programs for updating parameters) and/or hardware (e.g., Ethernet links between imaging device 104 and ablation device 102).

A planning module 122 may be stored in memory 116 and provide objectives, goals, and task sequences for performing a procedure. The planning module 122 may store thresholds and other criteria for comparison between measured and monitored parameters and the thresholds/criteria. The instrument or ablation device 102 may include or be part of a catheter, a guidewire, a probe, an endoscope, a robot, an electrode, a filter device, a balloon device, or other medical component for carrying out ablation. Ablation may include RF ablation, cryo-ablation, high intensity focused ultrasound (HIFU), laser ablation, microwave, etc. The ablation device 102 may be connected to and controlled by an ablation controller 126, although the controller functions may be handled using the workstation 112. The ablation device 102 and the controller 126 (which may include sensors or the like) are collectively referred to as an ablation system 124. The present principles provide adaptive control of ablation therapy that can be applied to any commercial device used for ablative therapy.

The ablation system 124 includes the ablation instrument 102 and the ablation controller 126. The ablation system 124 may be a part of the workstation 112 or may be an independent unit controlled using feedback generated by the workstation 112. A communication link 128 between the ablation system 124 and the US system 104 may be provided to enable feedback to the ablation system 124 and/or the imaging system 104 to more accurately estimate progress of the ablation and other parameters during a procedure.

In one embodiment, workstation 112 includes an image generation module 148 to display the measured parameters on or against real-time images collected during a procedure using the US system 104. It should be noted that the elastographic information (e.g., shear modulus, shear velocity, elasticity, etc.) is measured/monitored using US imaging; however, other imaging modalities may be employed in addition to or instead of US and may be adapted to measure these or other parameters to provide feedback for the ablation process. An image 134 may be modified or provided with an overlay including the elasticity or shear parameters and displayed on a display device 118 to provide a user with real-time feedback and demonstrate the progress of the ablation procedure. Another overlay or modification may be displayed on the display 118 to demonstrate goals or criteria in accordance with a plan stored in the planning module 122. For example, as tissue is being treated, a comparison or changes to the elasticity may be measured and displayed, and a real-time visual comparison may be made against areas to be treated as displayed in accordance with the plan stored in the planning module 122. In this way, an immediate understanding of remaining areas to be treated as well as treated coverage areas is contemporaneously known within a space or volume (subject) 131 in a patient.

Workstation 112 includes the display 118 for viewing one or more internal images 134 of the subject (patient) or volume 131. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

In one embodiment, the ablation process may have a manual aspect. In such an instance, currently selected imaging parameters and the resulting estimates of shear velocity and shear modulus may be displayed on display 118 to assist in guiding an operator. The operator may be provided with a mechanism (e.g., soft/virtual button) (interface 120) to override the automatically chosen imaging parameter values and permit manual operation with feedback from the ablation system 124 and/or the US system 104.

In accordance with the present principles, shear wave elastography (SWE) may be employed for monitoring ablation and, in particular, radiofrequency ablation (RFA). During RFA, the elastic properties of the tissue change, for example, a region being ablated first turns softer and then progressively stiffer. SWE resolves the extent of lesion formation during RFA, due to the dependence of the shear wave velocity on the underlying stiffness. A quantitative measure of the change in local stiffness can be obtained from parameters such as radiation force-induced displacement and Time-to-Peak (TTP) measured from the shear wave.

The parameter estimation and monitoring module 115 automatically varies the parameters of the pushing and tracking pulses of the US system 104 (e.g., for radiation force-induced displacement), based on inputs from the RFA system 124. Thus, at all stages of RFA, reliable velocity estimates (and hence, shear modulus estimates) can be obtained. If the RFA system 124 and the US system 104 are separate units, the link 128 may connect the RFA system 124 to the US system 104 (e.g., scanner console). Alternatively, both the RFA system 124 and US system 104 can be connected to or be part of the workstation 112, which collects data from both systems. In such a case, the estimated imaging parameters (i.e., pushing and tracking parameters, ablation control parameters, etc.) are communicated back to the respective system (e.g., US system 104 and/or the ablation system 124) to adjust the parameters.

Relevant parameters that may be extracted from the RFA system 124 may include, e.g., elapsed RFA time, cumulative deposited power, current temperature at RF probe tip, current temperature at each tine (electrode of the ablation instrument 102) along with location of that tine, etc. Appropriate imaging parameters (i.e., pushing and tracking parameters) may be selected by the parameter estimation and monitoring module 115 to vary at different times, based on inputs from RFA system 124 (e.g., using a pre-defined lookup table, program or other data structure or model 130). Additionally, the location in the tumor or tissue that is currently being imaged may also be a determining factor in the choice of imaging parameters. For example, imaging closer to the lesion boundaries may need different imaging settings compared to imaging a center of the RF lesion.

Figure 2:
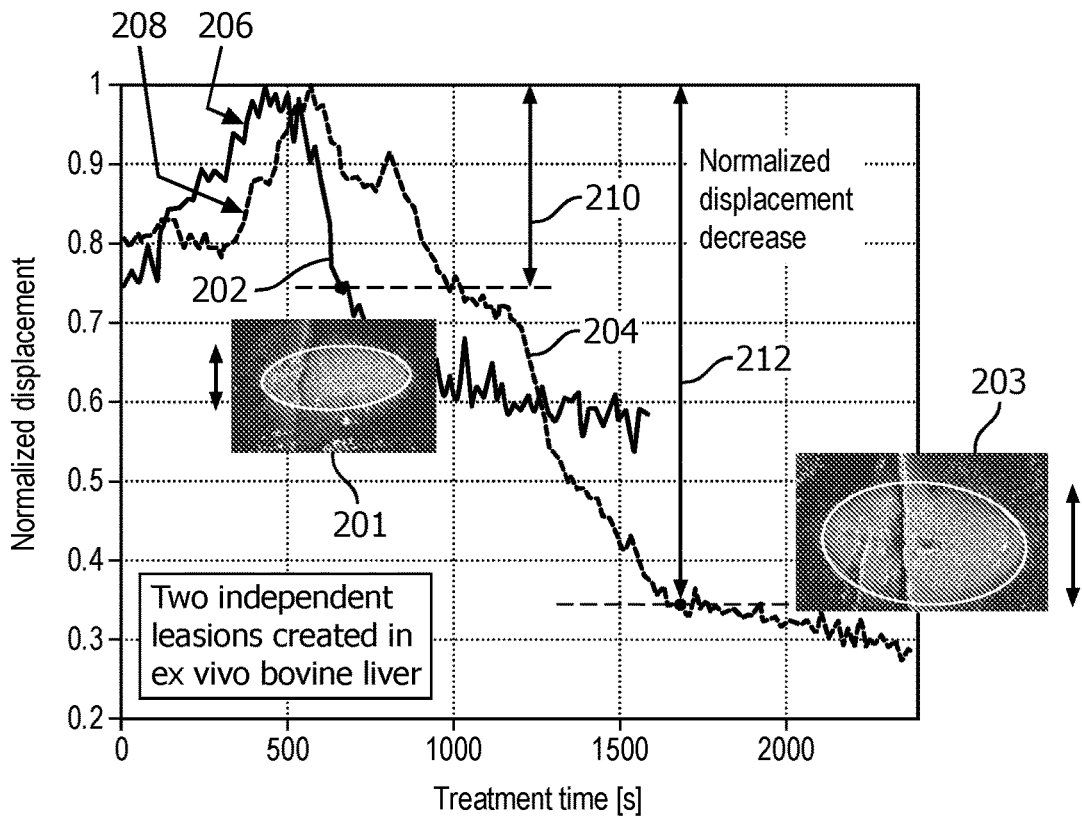
FIG. 2 is a graph plotting normalized displacement versus treatment time (sec.) for formation of two lesions in bovine livers showing softening and stiffening characteristics of ablated tissue.

Referring to FIG. 2, plots 202, 204 of normalized displacement versus treatment time (sec.) for bovine liver tissue demonstrate changes in parameters during lesion formation as therapy progresses. The normalized displacement plots 202, 204 illustrate initial softening followed by stiffening for independent lesions created in ex vivo bovine liver. Inset images 201, 203 represent the lesions visualized on gross pathology. The measurements were performed at a single location in the vicinity of a heating zone core during RF ablation in bovine liver. Two samples are depicted corresponding with plots 202 and 204. The trend of initial increase 206, 208 in displacement due to the softening is followed by a decrease 210, 212 in normalized displacement 210, 212 due to stiffening. The displacements 210, 212 have been normalized such that the peak value is always 1.

Figure 3:
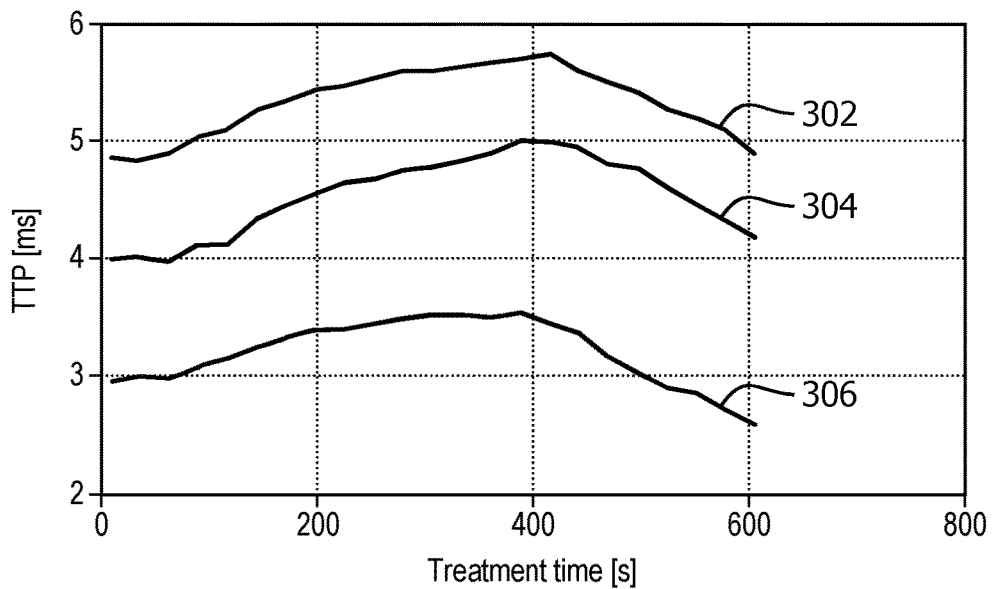
FIG. 3 is a graph plotting Time-to-Peak (TTP) (ms) versus treatment time (sec.) for three lesions in bovine livers showing softening and stiffening characteristics of ablated tissue.

Referring to FIG. 3, plots 302, 304 and 306, showing variation of Time-to-Peak as a function of treatment time in a plane parallel to and positioned 3 mm from an ablation electrode, are illustratively shown. The plots 302, 304 and 306 indicate lateral track positions (representative of distance) away from a push focus. The trend is consistent with that expected as the ablation progresses and a lesion is formed. Time-to-Peak variation displays the initial increase since the shear wave takes longer to reach the location followed by decrease due to the increased speed with stiffening.

Finite element simulations show how a temporal profile of the shear wave displacement curve versus propagation time is vastly different between soft (e.g., stiffness is about 1.33 kPa) and stiff (e.g., stiffness is about 8 kPa) tissue. The shear modulus for normal tissue is ~2 kPa, while it is close to 40-50 kPa or greater for ablated tissue, and thus the difference is significant. If a fixed sampling rate (or pulse repetition frequency (PRF)) that is appropriate for normal tissue is also used for ablated tissue, the displacement curve for ablated tissue will be undersampled, leading to an erroneous time-to-peak (TTP) measurement, and therefore, an inaccurate estimation of the shear modulus.

During ablation, once the temperature rises tissue initially softens and then eventually stiffens, the present principles use this knowledge to optimize the parameters so that the full integrity of the Time-to-Peak profile is maintained during the entire course of treatment. Based on knowledge of the expected variation of the Time-to-Peak profile, it would be useful to optimize a series of parameters, e.g., sampling rate (also known as pulse repetition frequency (PRF)) and spacing between the tracking locations, as a function of phase of treatment. These features may be implemented/selected on-the-fly during the treatment.

Stiffness of tissue decreases at the onset of heating due to tissue softening in response to temperature rise. As the tissue necrosis threshold temperature is reached, the tissue begins to harden and continues to do so with increased thermal exposure. By tracking this change, the therapy progress can be evaluated, and the end point can be determined. Tissue stiffness can be measured using shear wave imaging (or the Philips® ElastPQ™ feature on Philips® imaging systems). These techniques use acoustic radiation force to generate displacement and shear waves that are then tracked to extract stiffness information.

The real-time therapy monitoring and assessment techniques described herein are employed to enable modification of the therapy delivery parameters on-the-fly to optimize the therapy outcome. The present principles adjust the therapy parameters based on the shear wave/modulus and/or elastography measurements obtained from the ultrasound scanner in real-time. These elastography measurements can be measured over the entire treatment volume in multiple orientations and provide a more complete picture on the efficacy of treatment compared to conventional systems.

Figure 4:
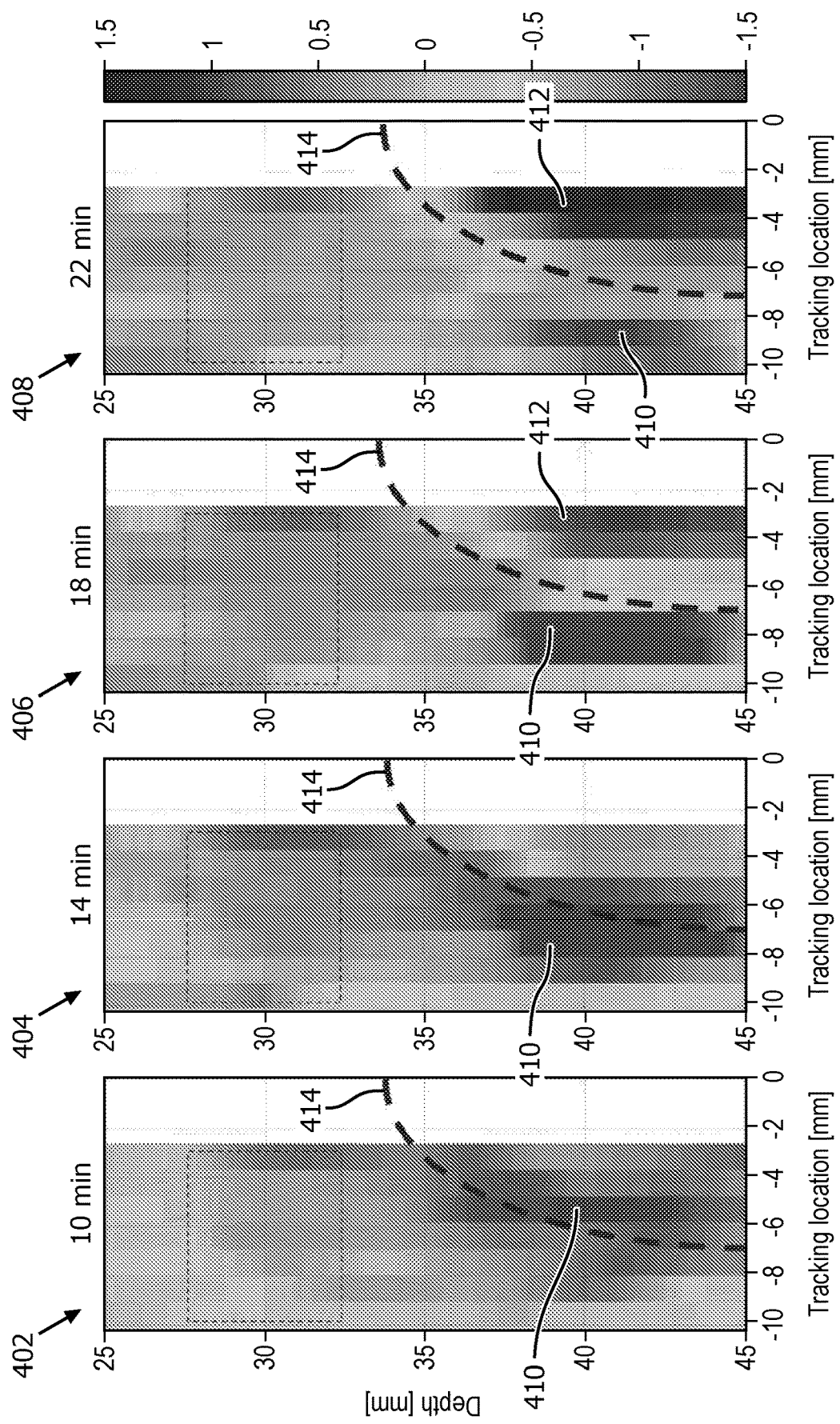
FIG. 4 shows plots of depth (mm) versus tracking location (mm) for four treatment times (10 min., 14 min., 18 min. and 22 min., respectively) for formation of lesions showing softening and stiffening characteristics of ablated tissue in accordance with one embodiment.

Referring to FIG. 4, graphs showing Time-to-Peak (TTP) based elasticity maps at different time points during a 22-min ablation are illustratively shown. A first map 402 shows elasticity after 10 minutes of ablation. A second map 404 shows elasticity after 14 minutes of ablation. A third map 406 shows elasticity after 18 minutes of ablation. A fourth map 408 shows elasticity after 22 minutes of ablation. Dark regions 410 moving to the left through maps 402-408 represent softening and dark regions 412 on the right represent stiffening of a lesion on an ex-vivo bovine liver. Dashed lines 414 represent a final thermal lesion boundary estimated from pathological evaluation.

In accordance with the present principles, experiments to illustrate the utility of elastographic measurements concurrent with lesion formation during RFA were performed by the present inventors. In these experiments, a track sequence included seven locations placed at a distance of 1.5 mm from a push beam. An ultrasound probe was oriented transverse to the ablation needle such that the ablation needle was in cross-sectional view on the ultrasound image. The ElastPQ™ window was carefully placed on the screen such that a left edge was 10 mm from an ablation tine. Raw ultrasound data in response to each push-track sequence was obtained every 15 seconds during the entire course of treatment. The data was processed to obtain Time-to-Peak (TTP) estimates during the entire course of ablation. The TTP values were obtained for each track line at 3 mm axial spacing. Thus, a spatial map was obtained illustrating the variation of TTP over the entire region undergoing thermal ablation therapy.

From the instantaneous TTP maps 402, 404, 406, 408, the TTP difference map is obtained by comparison with a first TTP frame acquired before heating. The TTP maps 402, 404, 406, 408 are shown at different time points. The ablation tine was at a depth of 45 mm and about 2 mm from the right edge of the image. Positive values on the maps indicate that the tissue is stiffening (since TTP has decreased in the current map) while negative values indicate it is softening (TTP has increased in the current map). With this convention, it can be seen that initially tissue softens (10 min) near the ablation tine and this softening progressively (14, 18 and 22 min) moves away from the right edge (close to tine) towards the left edge (close to the boundary of the lesion). At the same time, the right edge also starts to stiffen since it is close to the tine. The stiffening effect also progressively starts to move from right to left during the heating, i.e., from the tissue closer to the tines to the regions closer to the boundaries of the lesion that is forming.

Due to the large changes in shear modulus during lesion formation, different parameter sets for pushing and tracking are optimal at various stages of the lesion formation process. The parameters that can be optimized may include the pulse repetition frequency (PRF), the number of track locations, the spacing between the tracking beams, etc. However, the changes in these parameters may need to be made manually by the operator, based on the elapsed RF ablation time. This is inconvenient and also not optimal, since the decision to change these parameters may be made subjectively at the discretion of the user. Optimal values for these parameters have been empirically derived for different stages of the RFA process, from laboratory ex vivo experiments. These empirically-obtained parameter values can be related to different signatures of the RFA process (such as elapsed RFA time, cumulative output power, temperature at RF probe tip etc.). The use of such metrics in an automated fashion may be employed in accordance with the present principles to optimize the imaging (pushing and tracking) parameters in real-time, for optimal and accurate estimation of the shear velocity and shear modulus.

Figure 5:
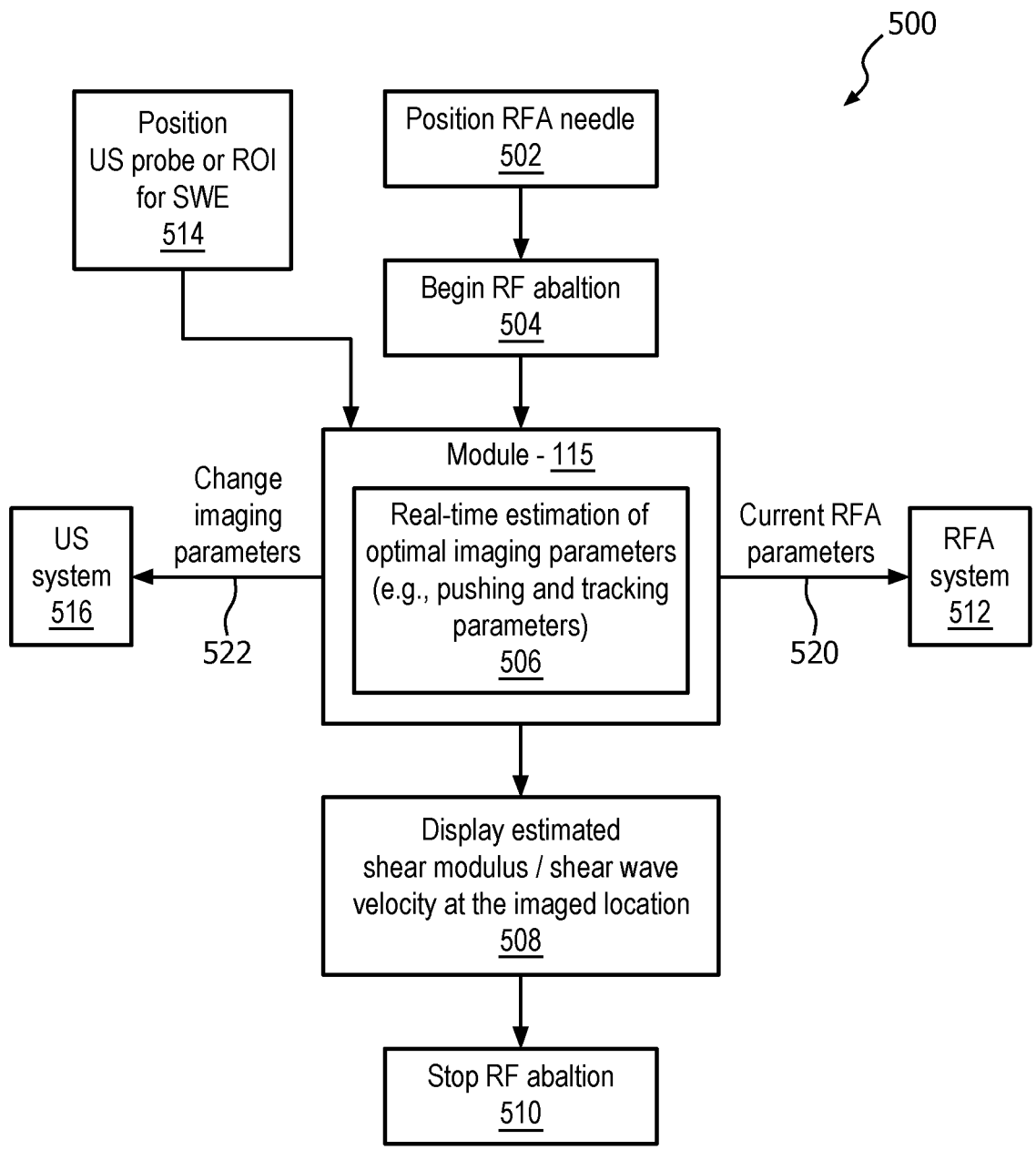
FIG. 5 is a block/flow diagram showing a system/method for performing ablation using feedback from an ablation device to change imaging parameters in accordance with useful embodiments.

Referring to FIG. 5, a block/flow diagram shows a system/method 500 which provides a communication link (feedback) 520/522 between an RFA system 512 and an US system 516 (through module 115). The communication link or connection 520/522 may include a combination of hardware and software to transfer and adjust parameters from the RFA system 512 to parameters for the US system 516. Parameters are optimized in real-time by the parameter estimation and monitoring module 115, which include an optimization module 506 along the link 520/522. Optimization module 506 optimizes parameters such as, e.g., the pulse repetition frequency (PRF), the number of track locations, the spacing between the tracking beams, or any other suitable parameter. For example, at the beginning of an RFA procedure, a parameter vector 'X' will be forwarded to module 506 along connection 520. From the RFA time elapsed (and/or output power/voltage or other input), the parameter vector will be changed accordingly (first to 'Y', then to 'Z' and so on). The values for 'X', 'Y', 'Z' may be empirically determined using a model, lookup table, formula or other estimation technique. In one embodiment, acoustic field measurements (e.g., shear wave parameters, moduli, etc.) may be performed while the system 500 is being used in conjunction with the RFA system 512 to measure the parameter values. For example, vector X may include the elapsed RFA time, cumulative deposited power, current temperature at RF probe tip, current temperature at each tine along with location of that tine, etc. These features may be updated by module 506 to output vector Y to connection 522 to the US system 516. The connections 520/522 may include an Ethernet cable, interfacing computer/circuit board, wireless communication links, etc.

In one embodiment, an RFA probe (102, FIG. 1) is inserted in tissue in block 502 to begin ablation in block 504. A US probe or region of interest (ROI) is also positioned and set for SWE in block 514. Appropriate RFA parameters are continuously read from the RFA system 512. The optimization module 506 proposes the optimal imaging settings (e.g., pushing and tracking parameter settings) to use at that instant, based on a combination of RFA settings and a current probe location. This may be determined by a stored plan or based on operator experience, etc. The module 506 takes shear wave imaging outputs into account when calculating new pushing and tracking parameters. The parameter estimation and monitoring module 115 further includes an image processing module 508 (module 148, FIG. 1) configured to display estimated shear modulus at a given location (e.g., either on a screen of the US system 516, on a standalone computer screen or on display 118). In addition, the imaging parameters that have been chosen at that instant (by the module 506) may also be displayed. The user can also override the automatic selection of the imaging parameters by entering his/her choice of parameters at any instant using interface 120 (FIG. 1).

At any time, the operator may move the US probe (or the ROI for SWE) to a different location (block 514). With knowledge of the spatial coordinates of the new location with respect to the ablation electrode, the imaging parameters will be updated accordingly. The ablation probe may also be repositioned to a new location in block 502. In block 510, ablation is stopped and the process ends when a goal or goals of the procedure are achieved or other criterion has been met. The system 500 permits more accurate and reliable monitoring of the RFA procedure by enabling accurate estimation of velocity and shear modulus in an automated manner. The present principles can be incorporated into the SWE module (e.g., Philips' ElastPQ™ and/or Shear Wave Imaging (SWI)) on an ultrasound platform.

Figure 6:
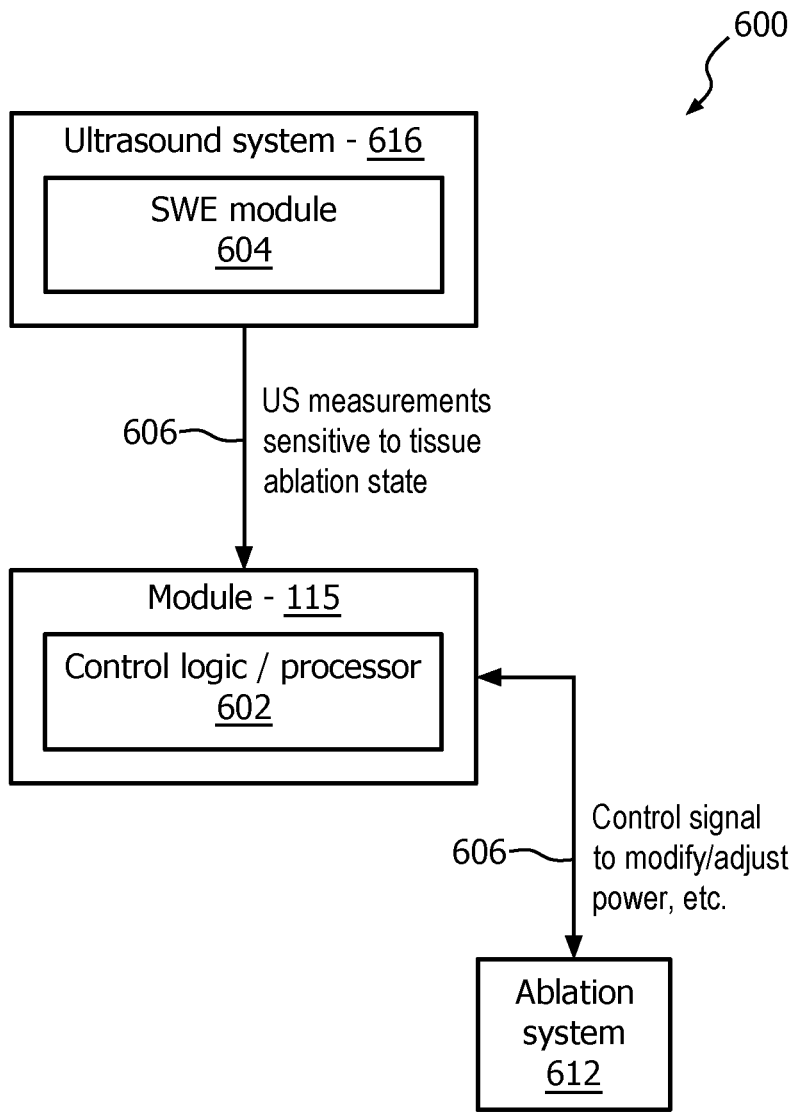
FIG. 6 is a block/flow diagram showing a system/method for performing ablation using feedback from an imaging device (elastographic information) to change imaging ablation device parameters in accordance with useful embodiments.

Referring to FIG. 6, another block/flow diagram shows a system/method 600 which provides a communication link or connection 606 to control an RFA system 612 based upon feedback (images and/or data) from an US system 616. The communication link or connection 606 may include a combination of hardware and software to transfer and adjust parameters of the RFA system 612 from parameters for the US system 616.

Current ablation therapy recipes rely on using the temperature (or impedance on some manufacturer's devices) readings from the device. The temperature readings are obtained from a sparse set of thermocouples located at the tip of the ablation electrode. The thermocouples provide local information about temperature rise at a central core of the lesion but lack valuable information on the therapy efficacy at the boundaries.

In accordance with the present principles, elastography imaging by the US system 616 provides a way to measure direct effects of therapy-induced changes in potentially multiple spatial dimensions encompassing an entire extent of the lesion. This comprehensive information, derived from the ultrasound scanner, could then be employed to optimize the power delivery output to various ablation electrodes that are used in a multi-electrode heating configuration.

This real-time information is then used to adapt the therapy delivery parameters by selectively increasing or decreasing the power, shutting some of the ablation electrodes off, etc. based on comprehensive measurements performed not only in the core of the lesion but also on the boundary of the lesion.

The US system 616 includes an ultrasound scanner, equipped with an elastography imaging/measurement module 604, that can obtain estimates of local stiffness properties in real-time during ablation. The parameter estimation and monitoring module 115 may further include an ablation control therapy device 602 that can dynamically change the power settings based on inputs from an independent source (e.g., images or data from the US system 616 and/or SWE module 604). The ablation control therapy device 602 may include control logic or a processor (e.g., workstation 112, FIG. 1)), which accepts the ultrasound-based measurements (e.g., shear modulus or elastography estimates) from the ultrasound system 616 and changes the power setting or mode of operation of an ablation generator module based on a pre-determined threshold that is met at one or multiple points on a spatial and/or temporal measurement map.

The data link or connection 606 (through module 115) permits measurements from the ultrasound system 616 to be transferred to the ablation device 612.

System 600 employs elastography measurements, e.g., obtained during RF ablation heating. In one embodiment, a modified version of the Elastography Point Quantification (ElastPQ™ mode) is employed, which may be on, e.g., an iU-22 ultrasound scanner equipped with a C5-1 probe. Although embodiments herein refer to particular types of measurements extracted from ultrasound, the present principles can be extended to any others that provide an outline of a lesion during therapy. Elastographic measurements (such as the point quantification (ElastPQ™) technique) made at different locations, both at the center of the lesion and near the lesion boundaries, are indicative of the progress of lesion formation. Given these real-time elastography-based measurements that reflect the current status of the therapy, selection of a few representative spatial points near a center and a periphery of the ablation zone can be performed, and the evolution of the TTP estimates can be monitored.

In one embodiment, the actual shear (or Young's) modulus values can be used as the input to the processor/control module 602. In another embodiment, change in TTP estimates can be employed. Other control parameters such as shear velocity, etc. are also contemplated. Elastography parameters may be utilized to update a treated region (pixels/voxels), compare with a planned treatment volume (PTV) and be fed to a processor associated with the ablation device 612. The processor or control module 602 can make a decision to stop power delivery or modify the power deposition profile in real-time by comparing the measurements with a preset threshold. An algorithm or program (130, FIG. 1) to modify the power could be based on a proportional-integral-derivative (PID) controller-type algorithm. Multiple spatial or temporal measurements may be employed in the controller's decision making logic.

In another embodiment, the system 600 may suggest additional location(s) for the ablation tines to ensure complete lesion formation. For example, the elastographic measurements can be made at a desired spatial location. If the measurements indicate that the tissue in that location has not been necrosed and is not likely to be necrosed with any change in ablation parameters with the current electrode position, the system 600 can suggest a new location for the tines closer to that tissue region. This information can be provided to the user via an interface (e.g., display 118, FIG. 1).

Figure 7:
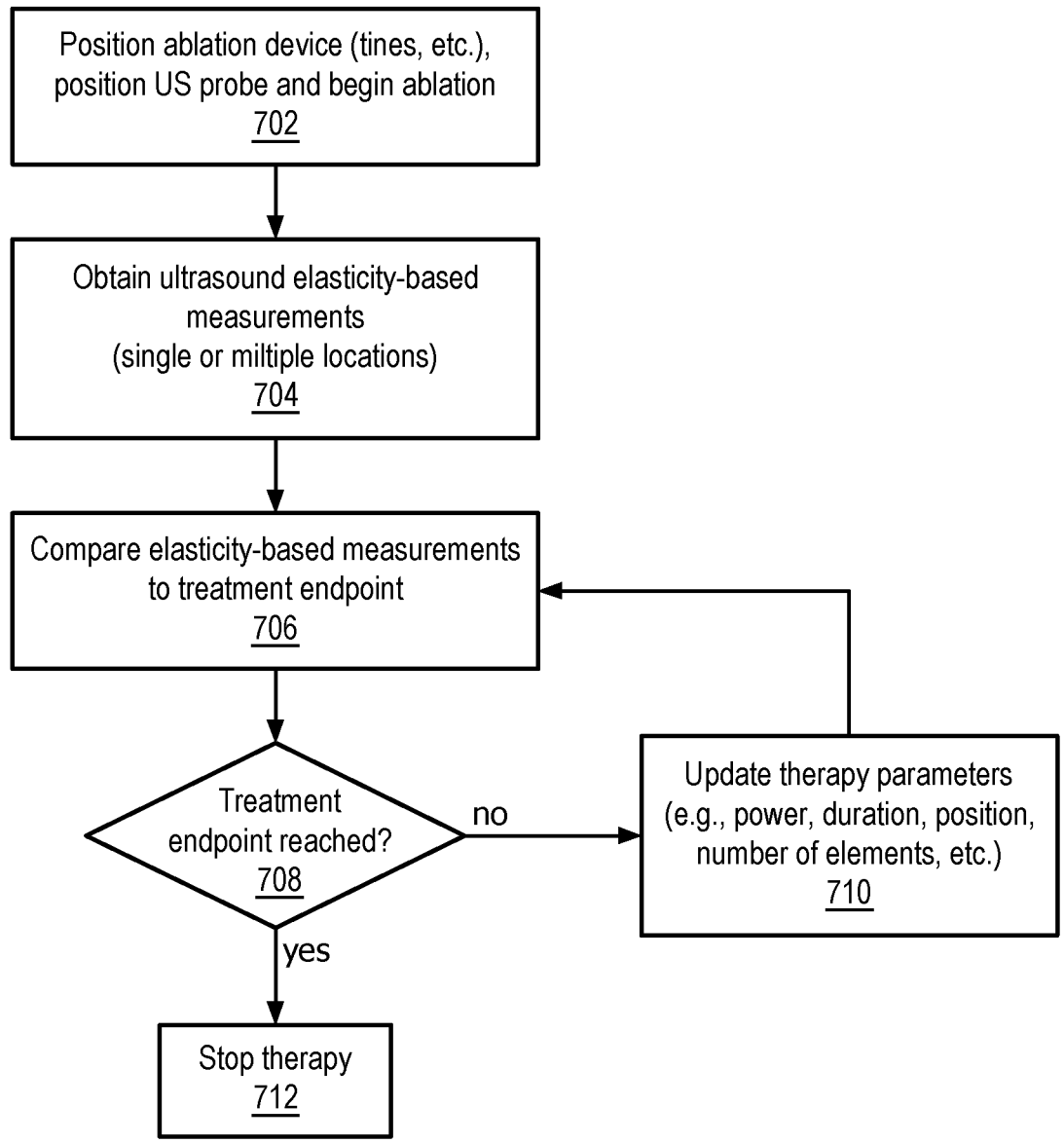
FIG. 7 is a flow diagram showing a method for performing ablation using feedback from an imaging device (elastographic information) to change imaging ablation device parameters for treatment in accordance with useful embodiments.

Referring to FIG. 7, a method for employing elastography feedback for an ablation procedure is illustratively shown in accordance with illustrative embodiments. In block 702, an ablation probe or tine(s) and an ultrasound probe are positioned, and ablation is commenced. In block 704, ultrasound elasticity-based measurements are made in a single or multiple locations about the ablated region. In block 706, the elasticity measurement(s) are compared to an endpoint. The endpoint may include a treatment endpoint or a prior measurement to evaluate progress. In block 708, a determination is made as to whether a treatment endpoint has been reached. If the treatment endpoint has been reached, then therapy is stopped in block 712. If the treatment endpoint has not been reached, therapy parameters are updated as needed in block 710 and the process returns to block 704. The parameters that are updated may include, e.g., power, duration, number of heating elements used, positioning of tines/heating elements, etc.

Figure 8:
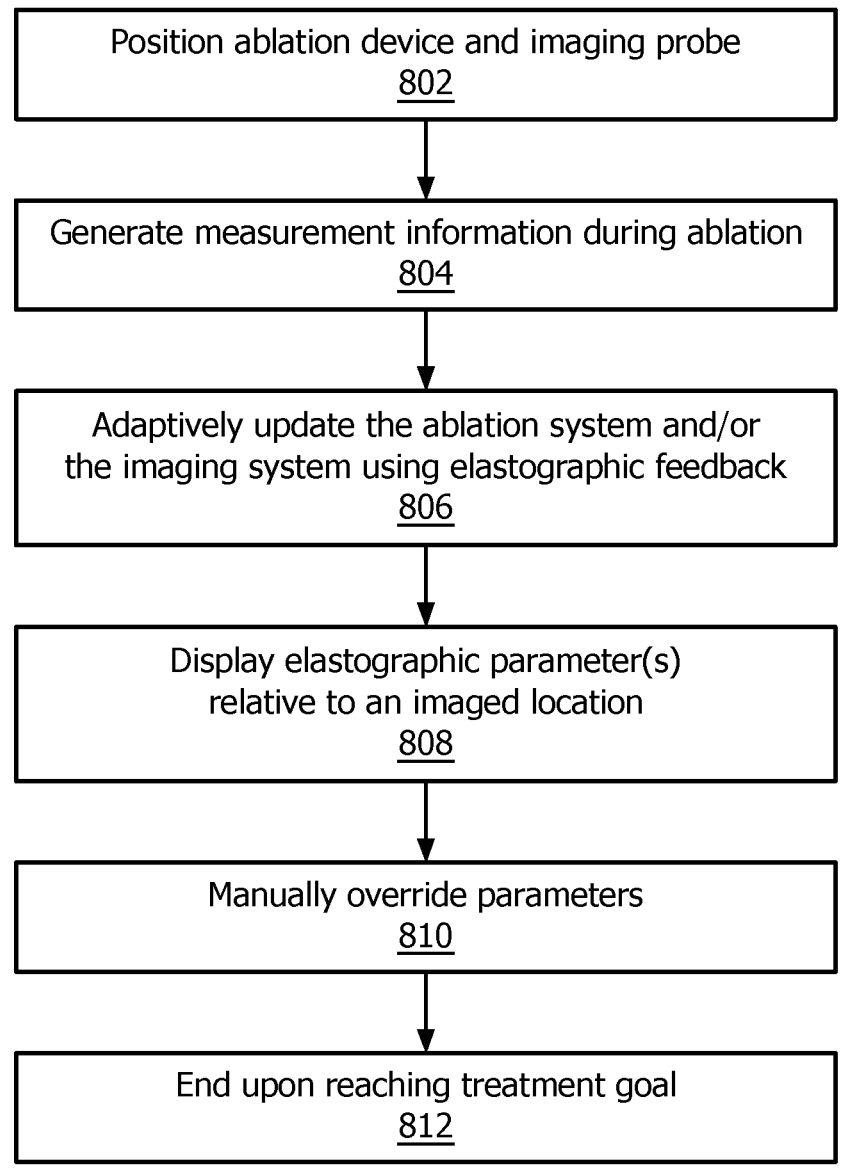
FIG. 8 is a flow diagram showing a method for performing ablation in accordance with useful embodiments.

Referring to FIG. 8, a method for performing ablation using elastographic feedback is illustratively shown. It should be understood that the elastographic feedback may be employed to adjust ablation device parameters, imaging parameters or both. The present principles may be intermittently applied depending on the procedure, measured threshold or other criteria. For example, feedback from imaging may be employed to change ablation parameters, ablation parameters may be employed to change imaging parameters and both changes may be employed during a same procedure, as needed.

In block 802, an ablation device and an ultrasound probe (or multiples thereof) are positioned in a subject at or near a region to be treated to begin ablation. If another imaging modality is employed, the US probe need not be positioned. In block 804, measurement information is generated as feedback during the ablation process including an elastographic parameter (e.g., shear wave, shear modulus, elasticity/stiffness, etc.) or related parameter. The measurement information includes information from the ablation device (ablation parameters), an ultrasound scanner (imaging parameters) or both. Feedback information may be provided by other sources or equipment as well. The measurement information of the ultrasound scanner may include one or more of shear modulus, Time-to-Peak estimates, shear velocity, etc. The measurement information from the ablation device may include one or more of elapsed ablation time, cumulative deposited power, ablation probe tip temperature and/or current temperature of an ablation tine parameter.

In block 806, at least one of imaging parameters of the ultrasound scanner and/or a control signal of the ablation device are adaptively updated in accordance with the feedback. The imaging parameters may include pushing and tracking parameters, which may further include one or more of pulse repetition frequency, number of track locations and/or spacing between tracking beams. The feedback from the ultrasound scanner may include stiffness measurements from one or more points on a spatial or temporal measurement map, wherein adjustments to the control signal employ the stiffness measurements from one or more points on the spatial or temporal measurement map. The control signal may be configured to adjust one or more of power settings of the ablation device and/or a mode of operation of the ablation device. The positioning, treatment duration and the configuration (number of elements, etc.) of the ablation device may also be controlled.

In block 808, the elastographic (shear wave or related) parameter is displayed relative to an imaged location on a display. The ablation parameters, imaging parameters or other information may also be displayed. In block 810, the ablation and/or imaging parameters may be manually overridden by manual changes through an interface.

In block 812, the ablation process is completed when a treatment goal is achieved. The target goal may include goals from a preoperative plan or other criteria.

In interpreting the appended claims, it should be understood that:
 a) the word "comprising" does not exclude the presence of other elements or acts than those listed in a given claim;
 b) the word "a" or "an" preceding an element does not exclude the presence of a plurality of such elements;
 c) any reference signs in the claims do not limit their scope;
 d) several "means" may be represented by the same item or hardware or software implemented structure or function; and
 e) no specific sequence of acts is intended to be required unless specifically indicated.

Having described preferred embodiments for systems and methods for adaptive ablation and therapy based on elastography monitoring (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for performing ablation, comprising:
 an ablation device configured to ablate tissue in accordance with control parameters and configured to take measurements during ablation;
 an imaging system configured to measure an elastographic related parameter indicative of ablation progress; and
 a parameter estimation and monitoring module configured to receive feedback comprising the measurements from the ablation device and/or the elastographic related parameter from the imaging system, and configured to adaptively adjust imaging parameters of the imaging system at different times during ablation based on the feedback, wherein the feedback provides information that tissue stiffness has changed, wherein the imaging parameters include: pulse repetition frequency, number of track locations, and/or spacing between tracking beams, and wherein the adjusted imaging parameters change a sampling rate for measurements from the ablation device and/or the elastographic relates parameter.

2. The system as recited in claim 1, wherein the imaging system is a shear wave elastography system which provides a pushing pulse that generates a shear wave to displace tissue and a tracking pulse to measure the tissue displacement and the imaging parameters include at least one of pulse repetition frequency of the pushing pulse and pulse repetition frequency, number of track locations, and spacing between tracking beams of the tracking pulse.

3. The system as recited in claim 1, wherein the parameter estimation and monitoring module adaptively adjusts imaging parameters of the imaging system at different times during ablation based on the measurements from the ablation device, and wherein the measurements from the ablation device include one or more of elapsed ablation time, cumulative deposited power, ablation probe tip temperature, and/or current temperature of an ablation tine parameter.

4. The system as recited in claim 1, wherein the parameter estimation and monitoring module adjusts the imaging parameters to empirically determined values from a lookup table or computer program.

5. The system as recited in claim 1, further comprising a display module configured to render the elastographic related parameter relative to an imaged location on a display.

6. A system for performing ablation, comprising:
 an ablation device configured to ablate tissue in accordance with a control signal;
 an imaging system configured to make elastographic measurements; and
 a parameter estimation and monitoring module configured to receive the elastographic measurements taken at selected points at a center and at a boundary of a lesion, as feedback from the imaging system and to adjust the control signal to control the ablation device to achieve therapy goals based on the elastographic measurements, wherein the feedback provides information that tissue stiffness has changed, and wherein the adjusted imaging parameters change a sampling rate for measurements for the elastographic relates parameter.

7. The system as recited in claim 6, wherein the control signal is configured to adjust one or more of power settings of the ablation device and/or a mode of operation of the ablation device.

8. The system as recited in claim 6, wherein the elastographic measurements include time-to-peak estimates and imaging parameters of the imaging system are controlled to maintain a time-to-peak estimation profile during ablation.

9. The system as recited in claim 6, wherein the feedback from the imaging system includes stiffness measurements from one or more points on a spatial or temporal measurement map.

10. The system as recited in claim 9, wherein adjustments to the control signal employ the elastographic measurements from one or more points on the spatial or temporal measurement map.

11. A method for ablation, comprising:
 positioning an ablation device and an ultrasound probe in a subject to begin ablation;
 generating measurement information as feedback during ablation including an elastographic related parameter, the measurement information including information from at least one of the ablation device and the ultrasound probe;
 adaptively updating imaging parameters of the ultrasound probe and a control signal of the ablation device in accordance with the feedback, wherein the feedback provides information that tissue stiffness has changed, wherein the imaging parameters include: pulse repetition frequency, number of track locations, and/or spacing between tracking beams, and wherein the adjusted imaging parameters change a sampling rate for measurements from the ablation device and/or the elastographic relates parameter; and completing ablation when the elastographic related parameters correspond to a predefined treatment criteria.

12. The method as recited in claim 11, wherein the step of adaptively updating imaging parameters of the ultrasound probe comprises updating the imaging parameters at different times during ablation based on the measurement information from the ablation device, and wherein the measurement information from the ablation device includes one or more of elapsed ablation time, cumulative deposited power, ablation probe tip temperature, and/or current temperature of an ablation tine parameter.

13. The method as recited in claim 11, further comprising displaying the elastographic related parameter relative to an imaged location on a display.

14. The method as recited in claim 11, further comprising overriding the imaging parameters and/or ablation control parameters by manual changes.

15. A parameter estimation and monitoring module configured to receive feedback comprising measurements from an ablation device and/or an elastographic related parameter from an imaging system, and configured to adaptively adjust imaging parameters of the imaging system at different times during an ablation process by the ablation device based on the feedback, wherein the feedback provides information that tissue stiffness has changed, wherein the imaging parameters include: pulse repetition frequency, number of track locations, and/or spacing between tracking beams, and wherein the adjusted imaging parameters change a sampling rate for measurements from the ablation device and/or the elastographic relates parameter.

16. A method for adaptively updating imaging parameters of an ultrasound inaging system comprising the steps of:

receiving feedback comprising measurements from an ablation device and/or an elastographic related parameter from an imaging system; and updating the imaging parameters based on the feedback, wherein the feedback provides information that tissue stiffness has changed, wherein the imaging parameters include: pulse repetition frequency, number of track locations, and/or spacing between tracking beams, and wherein the adjusted imaging parameters change a sampling rate for measurements from the ablation device and/or the elastographic relates parameter.

17. A system, comprising:

a processor; and a memory having stored thereon instructions that when executed by the processor cause the system to:

receive feedback comprising measurements from an ablation device and/or an elastographic related parameter from an imaging system, and adaptively adjust imaging parameters of the imaging system at different times during an ablation process based on the feedback, wherein the feedback provides information that tissue stiffness has changed, wherein the imaging parameters include: pulse repetition frequency, number of track locations, and/or spacing between tracking beams, and wherein the adjusted imaging parameters change a sampling rate for measurements from the ablation device and/or the elastographic relates parameter.

* * * * *